United States Patent [19]

Duinker

[11] 4,158,854
[45] Jun. 19, 1979

[54] APPARATUS FOR SCANNING AND PROCESSING INFORMATION OBTAINED BY SUCCESSIVELY IRRADIATING AN OBJECT FROM A PLURALITY OF DIRECTIONS

[75] Inventor: Simon Duinker, Bloemendaal, Netherlands

[73] Assignee: N.V. Optische Industrie "De Oude Delft", Netherlands

[21] Appl. No.: 839,882

[22] Filed: Oct. 6, 1977

[30] Foreign Application Priority Data

Oct. 15, 1976 [NL] Netherlands .......................... 7611419

[51] Int. Cl.² ................................................ H04N 5/32
[52] U.S. Cl. ..................................................... 358/111
[58] Field of Search ........................................ 358/111

[56] References Cited

U.S. PATENT DOCUMENTS 2,998,518  8/1961  Guntert ............................ 358/111 X
3,621,246  11/1971  Horsey et al. .................... 358/111 X

FOREIGN PATENT DOCUMENTS 1269640  12/1966  Fed. Rep. of Germany ........... 358/111

Primary Examiner—Richard Murray
Attorney, Agent, or Firm—O'Brien and Marks

[57] ABSTRACT

An apparatus for converting patterns of intensity-modulated scanning lines, each pattern representing an X-ray picture of an object when irradiated by a substantially flat beam of X-rays, into electrical signals, wherein such pattern is projected onto the target of a storage type camera tube having deflection means arranged for scanning said pattern along a plurality of scanning paths, each scanning path extending substantially transverse relative to the longitudinal axis of the image, and information derived from each one of said transverse scanning paths being individually processed.

7 Claims, 4 Drawing Figures

APPARATUS FOR SCANNING AND PROCESSING INFORMATION OBTAINED BY SUCCESSIVELY IRRADIATING AN OBJECT FROM A PLURALITY OF DIRECTIONS

This invention relates to an apparatus for scanning and processing information contained in picture formats formed by successively irradiating an object from a plurality of directions by means of a substantially flat beam of penetrating radiation elongated in one direction so as to obtain signal profiles for tomographic purposes, which apparatus comprises a two-dimensional detector surface, means for forming an optical image of this surface on the input of an electric image intensifier having an ouput screen for displaying the picture formats, and an electronic camera tube optically coupled to the display screen and including scanning means for scanning the display screen in accordance with a collection of scanning paths.

As described, for example, in Dutch patent application No. 76,05254 directed to image reconstruction, so-called signal profiles are used for constructing a tomogram. Each signal profile may be regarded as a series of transmission or absorption values measured along a line corresponding with a main face of the respective cross section of the object as irradiated by the flat beam of penetrating radiation produced by a suitable radiation source. As a result of such irradiation, a picture format is formed on the two-dimensional detector surface mounted opposite the object and optically displayed on the input of the electric image intensifier whose output screen is likewise optically displayed on the input screen of the electronic camera tube, such as a video camera tube. The height of the picture format corresponds with the "thickness" of the respective cross sectional image of the object, which thickness in turn is determined by the "thickness" of the flat beam of radiation as determined by the width of a slotted mask placed between the source of radiation and the object; the "image line" length of such a picture format is determined by the "fan angle" of the beam of radiation and is also determined by the length of the slotted mask. As a rule, an assembly comprising the source of radiation and the detector surface is rotated about an axis vertically extending through the respective cross section of the object, the rotation being essentially continuous.

In order to form the aforesaid signal profiles, each picture format (each instantaneous position of the assembly relative to the object corresponds with one picture format) is scanned and the signal profile corresponding with the respective position is derived from the image information thus obtained by integration.

One alternative method used in order to achieve one signal profile per picture format that is representative of the cross section of the object in the direction of the width of the format is that the picture formats be scanned "line-wise", or in a longitudinal direction, and integrated "column-wise", or in a lateral direction.

A number of drawbacks are inherent in such an method, as will be described hereinafter. These drawbacks make themselves particularly felt if it is tried to reduce the time required for obtaining a tomogram.

It is assumed that the assembly of radiation source and detector surface performs a complete revolution (360°) in 1 second; that a picture format having a width of 1 cm is read out along 25 image lines, at an image definition of 625 lines and a frame frequency of 50 Hz; and that the source of radiation is disposed at 75 cm and the detector surface at 25 cm from the axis of rotation.

On the basis of these assumptions it can be calculated that the time required for scanning an image line is 64 $\mu$sec. This means that a period of time, $t_{bk}=25\times 64=1.6$ msec is required for scanning each picture format. At a speed of revolution of 360° per second, i.e. 0.36° per msec, the screen describes an arc of $0.36\times 1.6=0.57°=10$ mrad, which corresponds with an arc length of $10^{-2}\times 250=2.5$ mm.

This means that a picture format associated with the beginning of the first image line scanned is shifted a distance of approximately 2.5 mm relative to the picture format associated with the beginning of the 25th image line scanned. In other words, the former picture format is advanced a period of time of approximately $t_{bk}$, i.e. approximately 1.6 msec, relative to the latter picture format. When, after scanning the respective 25 image lines, a column-wise integration is performed so as to produce the respective signal profile, in actual fact each time image line elements of different, relatively shifted picture formats are integrated, which will result in a certain degree of distortion in the ultimate tomogram. In other words, corresponding elements of successive image lines are integrated to obtain the value of the corresponding profile. This requires a separate storage device, each time elements spaced one image line period being added to each other. Such a separate device for temporarily storing the image line elements to be integrated constitutes an additional complication of the arrangement.

It is an object of the invention to eliminate the above drawbacks.

To this end, the apparatus according to the invention is characterized in that the scanning means are arranged for generating the scanning paths extending in directions transverse to the longitudinal or image line direction of the picture formats; and that information processing means are provided for separately processing the image information sensed in each of the scanning paths. This means that during the traversal of each scanning path, especially the portion thereof having a size and location as determined by the effective height and location of the picture format to be scanned, integration by means of an integrator takes place over such a scanning path. Thus a signal pattern is produced at the output of the integrator, which pattern is a collection of sum values that are each the result of such an integration performed over the respective portion of the scanning path. Such a signal pattern can be processed further by means of known apparatus, either in digital or in analog manner (parallelization, deconvolution, back-projection).

An apparatus constructed according to the invention further provides the important technical advantage that the interfering effect of scattered radiation on the image of the respective cross section of the object as formed on the detector surface can be eliminated in a simple and efficient manner. In the present case, the phrase "scattered radiation" is meant to refer to a combination of scattered X-radiation as occurring after irradiating the object, and of scattered light radiation as caused by the arrangement by means of which received X-radiation is converted to a video signal.

To this end, in accordance with an embodiment of the present invention, for each path trajectory traversed there is performed integration by a main integrator insofar as the portion of the trajectory is concerned that corresponds with the height and the location of the slot mounted in front of the detector surface, while over the portions of the trajectory corresponding with regions outside the slot there is performed integration by an auxiliary integrator, the results derived from the auxiliary integrator serving to eliminate the scattered radiation contribution from the result derived from the main integrator.

The invention will be described hereinafter by means of a description of two illustrative embodiments thereof, to which embodiments the invention is by no means limited, and with reference to the accompanying drawings, in which.

Figure 1:
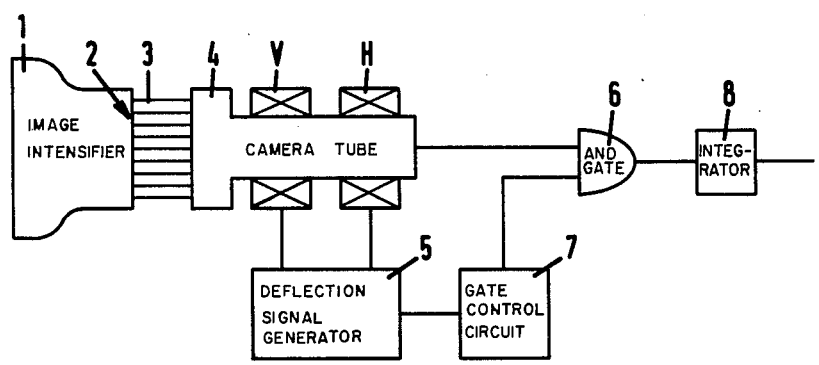
FIG. 1 shows a block diagram of a first embodiment.

To reconstruct a tomogram of a cross section of an object, it is standard practice to irradiate this object by means of a substantially flat, out-fanning beam of penetrating radiation, such as X-rays, such a beam being formed as a slotted mask is mounted between the source of radiation and the object to be irradiated. The assembly of the radiation source mounted on one side of the object and a detector surface of a detector device mounted on the other side thereof, is rotated about an axis vertically extending through the object so that this object is successively irradiated from a plurality of directions. Usually, the detector surface is optically coupled to an image intensifier or brightness intensifier adapted to form, on the display screen at its output end, an optical brightness-intensified image of the picture format projected on the detector surface, which picture format is indicative of an image of a cross section of the objct as associated with a specific instantaneous position of the radiation source relative to this object. The display screen is optically coupled through, for example, a fibre optics system to the input screen of an electronic camera tube with associated scanning means including a vertical deflection coil and a horizontal deflection coil, which scanning means serve to scan the input screen of the camera tube in accordance with a collection of scanning paths. As observed above, this scanning can be performed longitudinally along the length of the image so that, for example, 625 image lines are scanned per frame at a frame frequency of 50 Hz. As also observed above, this longitudinal scanning of the input screen entails a number of drawbacks. In accordance with the present invention, these drawbacks are eliminated as the scanning means associated with the electronic camera tube, particularly the means for controlling the scanning beam, are arranged for scanning the input screen of the tube, instead of longitudinal, laterally in a direction transverse to the image line direction, each time a separate integration being performed from each one of the transverse oriented scanning paths. In principle, this deflection control can be arranged for essentially sinusoidal scanning or, as preferred in the present case, for scanning in accordance with scanning paths extending essentially normal to the image line direction. Therefore, the persistence period of the display screen of the image intensifier is adapted to the period of time required for the complete scanning of a picture format.

Starting from a known detector arrangement having a screen of e.g. 340×200 mm, an image definition of 625 image lines corresponds with a height of 200 mm. When a picture format having a height of 8 mm, i.e. sufficient for an average "slice" of the object having a thickness of 4 to 5 mm, is chosen, a complete horizontal scanning over this height will require a number of 200/8=25 image lines. It is assumed that in the embodiment under consideration the time required for scanning such a picture format so as to obtain a signal profile will, just as in the example given above for a horizontal scanning, be 1.6 msec. When, as proposed in accordance with the present invention, such a picture format is scanned in accordance with scanning paths having, for example, a sinusoidal, and preferably a square wave, shape, which scanning paths extend essentially transverse to the horizontal direction, during each period of such a path there is scanned twice. Assuming, for example, that the resolution in the horizontal direction over the image line length of 340 mm is 680 image elements (corresponding with 0.5 mm of the screen or approximately 0.25 mm of the object), the scanning frequency amounts to $680 \times \frac{1}{2} \times 1/6 = 212$ period/msec, i.e. 212 kHz. When scanning in a direction transverse to the horizontal direction at such a high frequency, this implies that within a relatively short period of time T, which is 4.7 $\mu$sec at the frequency of 212 kHz, each time integration takes place twice. In other words, in the event of an integration performed each time within $\frac{1}{2}$T, i.e. within 2.3 $\mu$sec, the displacement of the detector surface and hence the aforesaid image distortion are negligible. It is observed, moreover, that the persistance periods of the detector surface (e.g. X-ray-sensitive fluoroscent screen) and the output screen of the image intensifier should be chosen less than or at best equal to the period of time required for scanning a picture format (1.6 msec in the embodiment under consideration).

When half a beam of radiation is employed, as described e.g. in Dutch patent application 76,05687, self-evidently the resolution in the horizontal direction is twice as high.

Figure 2:
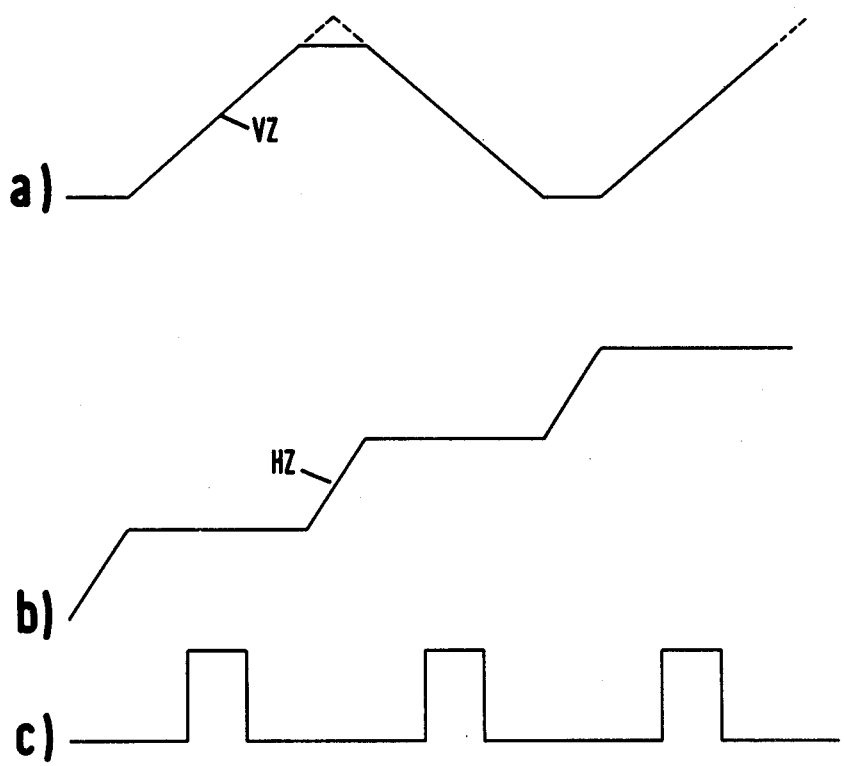
FIG. 2 shows a set of waveforms illustrating the organization and operation of the embodiment shown in FIG. 1.

The embodiment shown in FIG. 1 is organized in accordance with the idea underlying the present invention, inasmuch as an integration is performed over each scanning path extending transversely relative to the horizontal direction and only over a portion of the path corresponding with the width and location of the picture format to be scanned. In the configuration shown in FIG. 1, the image intensifier 1 has its output end provided with a display screen 2. This screen 2 is optically coupled through a fibre optics system 3 to the input screen of the electronic camera tube 4. This tube 4 is provided with scanning means including a vertical deflection coil V and a horizontal deflection coil H, which scanning means serve to scan the input screen of the camera tube 4 with a collection of scanning paths. As stated above, this scanning may be performed longitudinal so that, for example, 625 image lines are scanned per frame at a frame frequency of 50 Hz. As also stated above, this longitudinal scanning of the input screen entails a number of drawbacks. In accordance with the present invention, these drawbacks are eliminated as the scanning means associated with the electronic camera tube, particularly the deflection generator for controlling the scan beam, are arranged for scanning the input screen of the camera tube, instead of longitudinally, in directions transverse to the longitudinal direction of the image, with a separate integration being performed over each one of the transversely oriented scanning paths. In the present embodiment, the deflection signal generator is arranged in known per se manner so that the scan beam describes a square wave path on the input screen of camera tube 4. To this end, deflection signals having the waveforms VZ and HZ shown in FIG. 2 are applied to deflection coils V and H respectively. The output of the camera tube 4 is connected to one input of an AND gate 6. The other input of this gate 6 is connected to a gate control circuit 7. The output of gate 6 is connected to an integrator 8. Each time the gate control circuit 7 produces a gating signal (FIG. 2c), the gate 6 is opened to pass the output signal of camera tube 4 to integrator 8 so as to be integrated. The gate control circuit 7 is arranged so that, during the scanning of a scanning path extending transverse to the horizontal direction, a gating signal is produced for a portion of the scanning path corresponding with the width and location of the picture to be scanned.

The invention and hence the embodiment described above render it possible to construct a tomogram of a plurality of superimposed cross sections of the object in a simple manner. In that case, suitably arranged slotted masks are used to project on the input screen of the image intensifier an image configuration corresponding with the respective superimposed cross sections of the object, as a result of which a corresponding number of superimposed picture formats is formed on the display screen, such as 2, at the output end of the image intensifier. By scanning each scanning paths extending transverse to the horizontal direction, all the superimposed picture formats are scanned. The output of the camera tube 4 is connected to a plurality of AND gates such as gate 6, each of these gates having its output connected to an associated intergrator such as 8. A separate gate control circuit such as 7 is provided for each AND gate. Self-evidently, the operation of the gate control circuits is synchronized with the operation of the deflection signal generator 5. The control of these gates can be selected so that the signals produced at the output of the camera tube fully or partially overlap each other in time.

Figure 3:
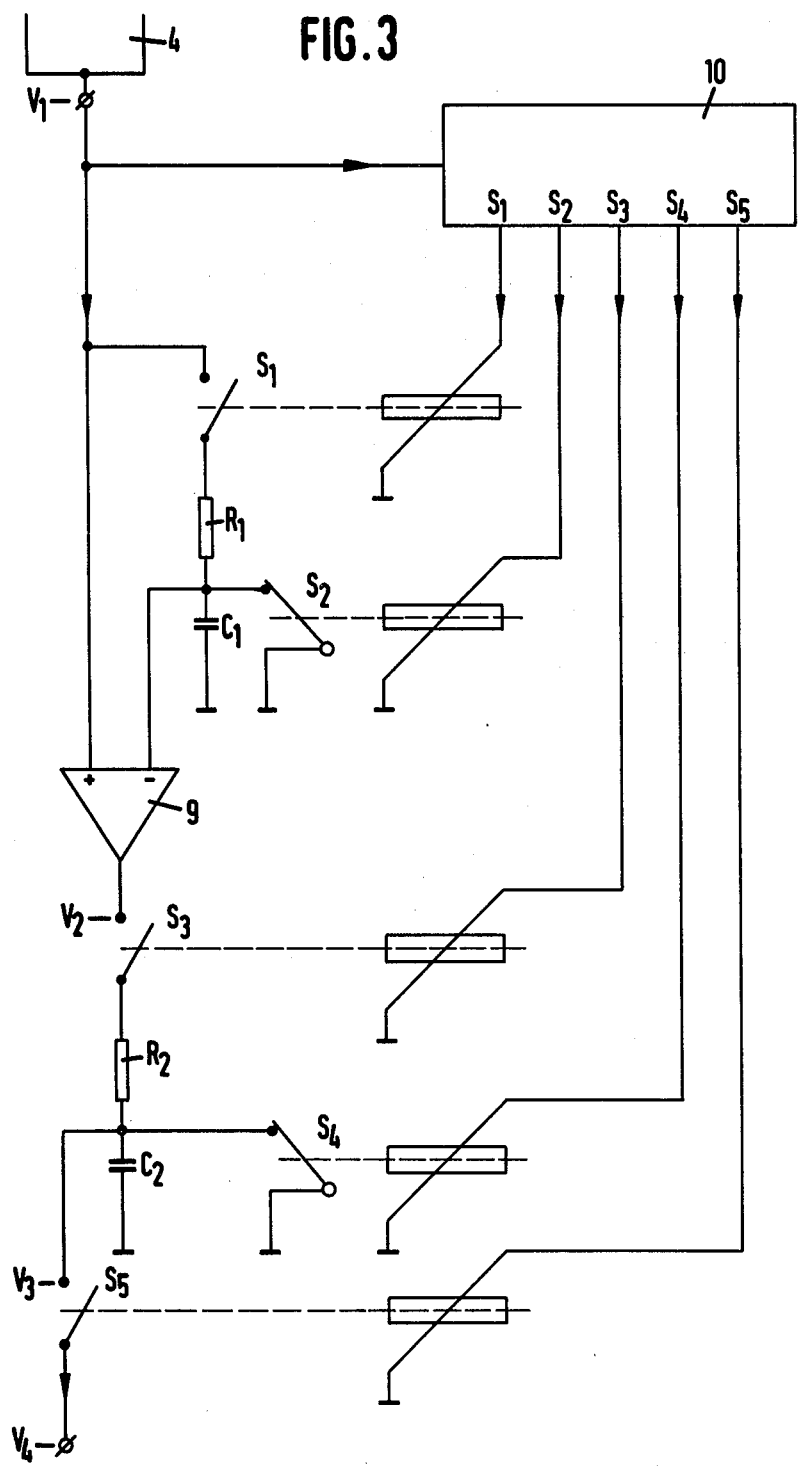
FIG. 3 shows a block diagram of a second embodiment.
Figure 4:
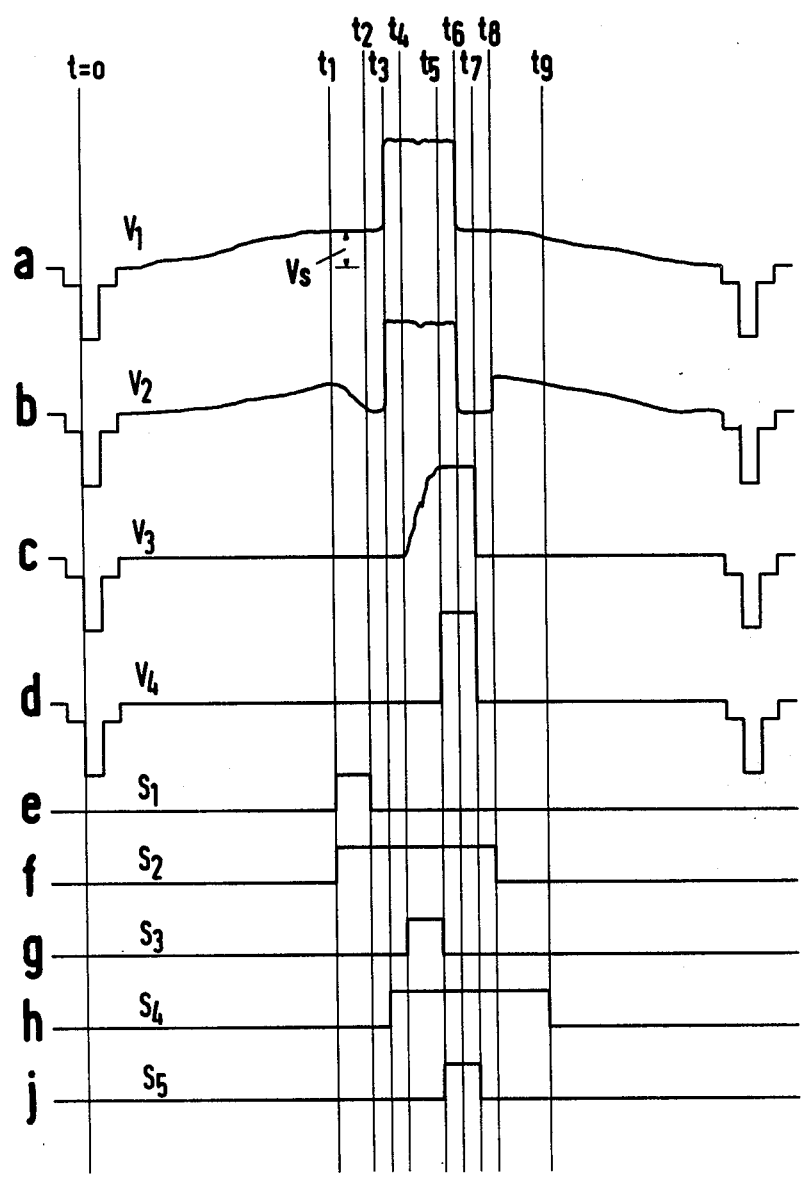
FIG. 4 shows a set of waveforms illustrating the organization and operation of the embodiment shown in FIG. 3.

As observed above, in accordance with a further aspect of the present invention the interfering effect of scattered radiation on the image of the cross section of the object as formed on the detector surface may be eliminated in a simple and efficient manner. FIG. 3 shows an embodiment serving this purpose, the operation and organization of which is described with reference to FIG. 4. The output of the camera tube 4 (FIG. 1) is connected to one input of a differential amplifier 9. The other input of this differential amplifier 9 is connected to the output of an auxiliary integrator comprising a resistor $R_1$ and a capacitor $C_1$. The output of the camera tube 4 is also connected to a switching signal generator 10 responsive to a start stimulation chosen in the output signal of camera tube 4 to each time produce a predetermined sequence of control signals $s_1$–$s_5$, which control signals are determined as to duration as well as to moment of occurrence. Each of these control signals is adapted to control an associated bistable switch unit $S_1$–$S_5$. The output of the differential amplifier 9 can be connected through the switch unit $S_3$ to a main integrator comprising a resistor $R_2$ and a capacitor $C_2$. The output of this main integrator can be connected through the switch unit $S_5$ to the output of the apparatus to which additional processing means (not shown) can be connected.

FIG. 4a shows an image signal $V_1$ as can be produced, for example, at the output of camera tube 4 during a scanning path extending transverse to the horizontal direction. From the significant image signal portion produced during interval $t_3$–$t_6$ there is chosen a portion lying between points of time $t_4$ and $t_5$ that is eligible for reconstruction. The choice of thickness of the object slice and relative position are important here. It is assumed that this significant image signal portion contains an undesired scattered radiation contribution, which contribution is represented in FIG. 4a by $V_S$. The effect of the scattered radiation will be substantially equal within and just outside interval $t_3$–$t_6$. Use is made of this presumption to achieve the desired scattered light radiation compensation. By measuring the scattered radiation contribution during an interval such as $t_1$–$t_2$ just outside interval $t_3$–$t_6$ and subtracting the thus-measured value from the image $V_1$ during the interval $t_2$–$t_8$, an image signal $V_2$ (FIG. 4b) is obtained that is free from the undesired scattered radiation contribution. By integrating the resultant image signal during the interval $t_4$–$t_5$ and retaining it until point of time $t_7$, a signal $V_3$ as shown in FIG. 4c is achieved that is eligible for further processing. During interval $t_5$–$t_7$ this signal $V_3$ can be passed to the additional processing means, as schematically shown in FIG. 4d by signal $V_4$. FIGS. 4e–4j show the aforesaid sequence of control signals as produced by the switching signal generator 10 in response to a start stimulation. Such a start stimulation, preferably occuring at the point of time $t_0$, can be derived, for example, from the first negatively directed edge of the horizontal sync pulse for the respective image line. Control signals $s_1$ occurring during interval $t_1$–$t_2$ actuates switching unit $S_1$ to connect the auxiliary integrator to the output of camera tube 4. Control signal $s_2$ (FIG. 4f) produced concurrently with control signal $s_1$ actuates switching unit $S_2$ to break the short circuit of capacitor $C_1$. As a result of the occurrence of the two control signals $s_1$ and $s_2$, this auxiliary integrator is operative to measure and integrate the scattered radiation contribution $V_S$ during interval $t_1$–$t_2$. As during interval $t_1$–$t_8$ the capacitor $C_1$ is no longer short-circuited, this integration result as derived from the auxiliary integrator is retained throughout this interval and can be subtracted from the image signal portion occurring during interval $t_4$–$t_5$. This interval $t_4$–$t_5$ is determined by control signal $s_3$ (FIG. 4g), which signal operates switching unit $S_3$ to establish the connection between the output of the differential amplifier 9 and the main integrator comprising resistor $R_2$ and capacitor $C_2$. Control signal $s_4$ produced concurrently with control signal $s_3$ actuates switching unit $S_4$ to break the short circuit of capacitor $C_2$. In this situation the main integrator is operative to integrate the output signal of differential amplifier 9 over the interval $t_4$–$t_5$. The control signal $s_5$ (FIG. 4j) occurring during interval $t_5$–$t_7$ actuates switching unit $S_5$ to permit the intergrated output signal to be passed on for further processing.

The switching signal generator 10 may be composed, for example, of a configuration of monostable flip-flop responsive to the start stimulation to produce the sequence of control signals $s_1$–$s_5$.

An output signal $T_4$ obtained by means of the embodiment described above may be further processed in a known digital or analog manner.

I claim:

1. An apparatus for scanning and processing information contained in picture formats elongated in a longitudinal direction and formed by successively irradiating an object from a plurality of directions with a substantially flat beam of penetrating radiation so as to obtain signal profiles for tomographic purposes, the apparatus comprising a two-dimensional detector surface, means for optically forming an image of said surface on the input of an electronic image intensifer including an output screen for displaying the picture formats, an electronic camera tube optically coupled to said screen and including scanning means for scanning said output screen in a pattern of scanning paths, said scanning means being arranged so as to cause said scanning paths to extend in a direction substantially traverse relative to the longitudinal direction of the picture formats and information processing means provided for separately processing the image information obtained during each of said scanning paths.

2. An apparatus as claimed in claim 1 wherein said scanning means is arranged to generate scanning paths extending in a direction essentially normal to said longitudinal direction.

3. An apparatus as claimed in claim 2 wherein said information processing means includes an integrator connected through a controllable switching means to the output of said camera tube, said switching means being controlled by a control device operative to render said switching means conductive during time intervals that each correspond with a scanning path segment the size and location of which is determined by the effective width and location of the respective picture format being scanned.

4. An apparatus as claimed in claim 3 wherein said information processing means includes a number n of said integrators, n being in integer greater that 1 and being equal to the number of superimposed partly overlapping picture formats to be scanned each of said integrators being connected to the output of said camera tube through an individual controllable switch unit.

5. An apparatus as claimed in claim 3 wherein an auxiliary integrator is associated with each of said integrators, the results derived from the auxiliary integrators being used to eliminate a scattered radiation contribution from the result derived from the integrator.

6. An apparatus as claimed in claim 5 wherein the integrator and the associated auxiliary integrator are alternately operative so that the integration performed by the main integrator is preceded by a measurement and integration of the scattered radiation contribution.

7. An apparatus as claimed in claim 1 wherein the persistence of the display screen of said image intensifier is adapted to the period of time required for a complete scanning of a picture format.

* * * * *